United States Patent
Swain et al.

(10) Patent No.: US 6,488,817 B1
(45) Date of Patent: Dec. 3, 2002

(54) PURIFICATION OF HYDROFLUOROCARBONS

(75) Inventors: Charles Francis Swain, Williamsville, NY (US); Rajiv Ratna Singh, Getzville, NY (US); Hang Thanh Pham, Amherst, NY (US)

(73) Assignee: AlliedSignal Inc., Morris Township, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,757

(22) Filed: Mar. 31, 1998

(51) Int. Cl.$^7$ ............................... B01D 3/36; B01D 3/42
(52) U.S. Cl. ............................. 203/74; 203/75; 203/77; 203/78; 203/80; 203/67; 203/DIG. 11; 570/178
(58) Field of Search ................ 203/73–75, 77–78, 203/80, 67, DIG. 11, 2, 3; 570/177, 178

(56) References Cited

U.S. PATENT DOCUMENTS

| | | | |
|---|---|---|---|
| 5,346,595 A | | 9/1994 | Clemmer |
| 5,470,442 A | * | 11/1995 | Mahler et al. ............. 203/66 |
| 5,523,015 A | * | 6/1996 | Tsuda et al. ............... 203/39 |
| 5,707,497 A | * | 1/1998 | Galland et al. ............ 203/75 |
| 5,785,822 A | * | 7/1998 | Cerri et al. ................ 570/178 |

* cited by examiner

*Primary Examiner*—Virginia Manoharan
(74) *Attorney, Agent, or Firm*—Colleen D. Szuch

(57) ABSTRACT

A process for the purification of difluoromethane comprising:
(a) subjecting a mixture comprising at least difluoromethane (HFC-32) and dichlorodifluoromethane (CFC-12) to a first distillation step in which a majority of either CFC-12 or HFC-32 is concentrated in a first distillate and a majority of the other component is concentrated in a first bottoms; and
(b) subjecting the first distillate in step (a) to at least one additional second distillation step conducted at a different pressure in which a majority of the component concentrated in said first distillate is concentrated in a second bottoms and in which the other component is concentrated in a second distillate; and
(c) recovering purified HFC-32 from one of said first or second bottoms.

18 Claims, 1 Drawing Sheet

PURIFICATION OF HYDROFLUOROCARBONS

FIELD OF INVENTION

The present invention relates broadly to the purification of hydrofluorocarbons. More specifically, the present invention relates to the separation of an azeotrope of dichloromethane (HFC-32) and dichlorodifluoromethane (CFC-12).

BACKGROUND OF THE INVENTION

Difluoromethane (HFC-32) is a hydrofluorocarbon developed to replace ozone-depleting hydrochlorofluorocarbons (HCFCs) or chlorofluorocarbons (CFCs) refrigerants/refrigerant blends. During the production of HFC-32, certain by-products are formed, including CFC-12, which is of particular interest herein. It has been found that CFC-12 and HFC-32 form a low-boiling azeotrope in the distillation of HFC-32.

Such an azeotropic cannot be separated using conventional distillation techniques. Furthermore, alternative methods of separating CFC-12 from HFC-32 such as extraction, extractive distillation, or absorption introduce higher costs and additional components to the purification process.

Although further recovery of HFC-32 tends to be difficult, it is nevertheless necessary to maintain high yields. For example, if no additional recovery of HFC-32 is performed on an azeotropic distillate containing about 9.2 wt % CFC-12 (as would be obtained through economical, high pressure distillation), then an HFC-32 yield loss of at least 10% can be expected. In other words, without further recovery, the HFC-32 yield would be less than 90%.

Therefore, a need exists for a process which recovers HFC-32 in high yield from the CFC-12/HFC-32 azeotropic distillate, but which does not involve costly and complex distillation techniques and apparatus. The present invention fulfills this need among others.

DESCRIPTION OF THE INVENTION AND PREFERRED EMBODIMENTS

Figure 1:
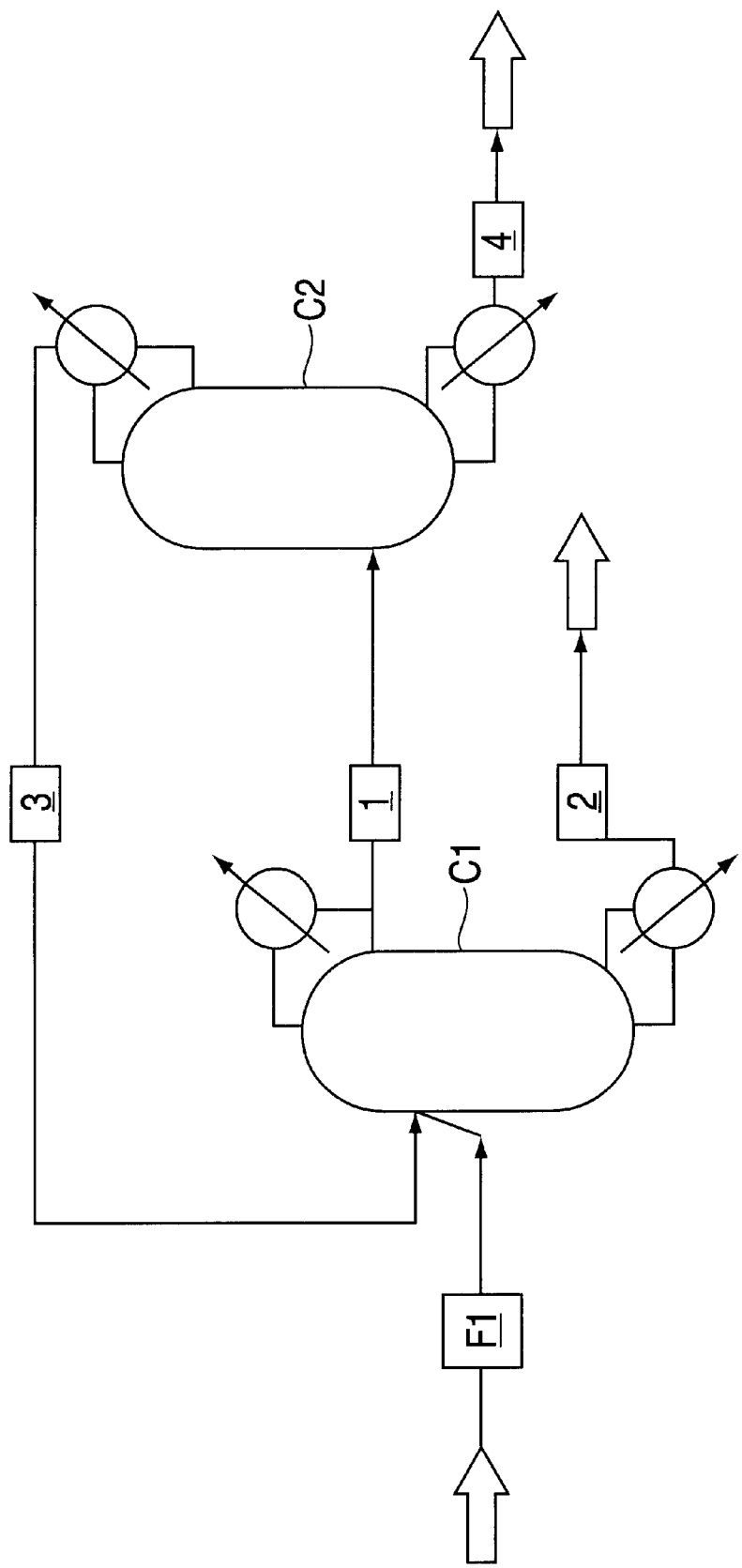
FIG. 1 shows the preferred embodiment of the distillation system for separating the HFC-32/CFC-12 azeotrope.

The present invention provides for high yield recovery of HFC-32 from a mixture containing CFC-12 using swing distillation in which the mixture is distilled at various pressures to effect separation. Distilling the mixture at different pressures effects separation because it has been found that the composition of the HFC-32/CFC-12 azeotrope changes sign ificantly upon a change in pressure. Although some change in an azeotrope's composition can be expected with a change in pressure, it has been found that the composition of the HFC32/CFC-12 azeotrope changes approximately 20 wt % from atmospheric pressure to about 200 psia. This is more than one skilled in the art would expect.

Such a significant composition differential facilitates separation because either HFC-32 or CFC-12 will tend to concentrate in the distillate during distillation at one pressure, and then, upon distillation of the distillate at a different pressure, will tend to concentrate in the bottoms. This way, the component can be removed from the mixture through the bottoms.

Additionally, since these pressures are within the operating parameters of conventional distillation equipment, the process of the present invention can be practiced using existing equipment with little or no modification.

One aspect of the present invention is a process for the purification of HFC-32 from a mixture of HFC-32/CFC-12. The process comprises: (a) subjecting a mixture comprising at least HFC-32 and CFC-12 to a first distillation step in which a majority of either CFC-12 or HFC-32 is concentrated in a first distillate and a majority of the other component is concentrated in a first bottoms; and (b) subjecting the first distillate in step (a) to at least one additional distillation step conducted at a different pressure in which a majority of the component concentrated in said first distillate is concentrated in a second bottoms and in which the other component is concentrated in a second distillate; (c) optionally recycling said second distillate to said first distillation step at least once; and (d) recovering purified HFC-32 from one of said first or second bottoms.

Another aspect of the present invention is a process for further recovering HFC-32 from an azeotropic distillate comprising HFC-32/CFC-12 as obtained from the distillation of HFC-32 by subjecting the azeotrope distillate to pressure swing distillation to recover HFC-32 in yields of no less than about 90%.

The process of the present invention may be performed using batch distillation or continuous distillation. In large scale commercial production, continuous distillation is preferred. A preferred continuous distillation system is shown schematically in FIG. 1. Feed material (F) containing less than the low pressure azeotropic concentration of CFC-12 is fed into the first distillation column (C-1) and operated at low temperature, preferably close to atmospheric pressure. At such low pressures, the azeotrope is relatively high in CFC-12 concentration. Consequently, the overhead distillate (1) from the low pressure distillation column (C-1) is greatly enriched with CFC-12. Bottom product (2) from the first low pressure distillation column (C-1) contains HFC-32 product with very low CFC-12 concentration.

The overhead distillate (1) from the first distillation column (C-1) is fed into a second distillation column (C-2) operating at a relatively high pressure. At such a high pressure, the amount of CFC-12 in the azeotrope drops dramatically. The pressure difference between the first and second distillation steps is sufficient to result in a change in composition of the azeotrope of CFC-12 and HFC-32 of at least 10 wt %, more preferably, at least a 15 wt %, and, even more preferably, at least 20 wt %. Consequently, distillate (3) contains a relatively high concentration of HFC-32, while, the bottoms (4) contains a relatively high concentration of CFC-12.

Optionally, distillate (3) from the second high pressure distillation column (C-2) is recycled to the first distillation column (C-1) to recover HFC-32 for high yield.

One skilled in the art will appreciate that modifications to the above system are possible. For example, the first distillation column (C-1) may be operated at a relatively high pressure, and distillate therefrom distilled at relatively low pressure in the second distillation column (C-2). Optionally, as above, the distillate from the second distillation column (C-2) may be recycled to the first distillation column (C-1). This configuration may be preferred for feed compositions having a concentration of CFC-12 at or above CFC-12 azeotropic concentration as discussed below.

The precise configuration of whether the feed is first introduced into the high or low pressure column depends upon the feed composition and the process economics. As a general rule, feed composition must contain less than the azeotropic amount of CFC-12 at a particular pressure to remove a majority of the CFC-12 as distillate. If the CFC-12 concentration in the feed is the same or greater than the azeotrope composition at the pressure of the low pressure column, then it must be fed into the high pressure column so that the majority of the CFC-12 can be removed efficiently as bottoms from the high pressure column. For example, if the low pressure distillation is conducted at atmospheric pressure, which corresponds to a CFC-12 azeotropic concentration of 29 wt %, then feeds having a CFC-12 concentration below 29 wt % should be introduced in the low pressure distillation. However, any feed having a composition at or above 29 wt % CFC-12 should be fed to the high pressure distillation. One skilled in the can readily determine the CFC-12 azeotropic concentrations for the low pressure distillation and compare this value to feed composition to determine whether the feed should be introduced into the low or high pressure distillation step.

Rather than performing the process of the present invention using continuous distillation, it may be preferable in certain circumstances, for example, in pilot plants, to perform the process using batch distillation. In batch distillation typically a single distillation column is used. The mixture may be fed, for example, into a distillation column operating at high pressure. The distillate is then collected and refed into the column after it has been cleaned. This time, the column is operated at a low pressure. The purified HFC-32 is then recovered from the bottoms of the still operating at low pressure.

Whether the distillation process is continuous or batch, the pressure at which the distillations are conducted preferably are such that conventional distillation apparatus can be used. To this end, the low pressure distillation is conducted at a pressure preferably no greater than about 40 psia, more preferably between about 5 and about 30 psia, and most preferably at about atmospheric pressure. The high pressure distillation is conducted at a pressure preferably between about 50 and about 400 psia, more preferably between about 100 and about 300 psia, and most preferably between about 175 and about 225 psia.

The temperatures at which these distillations are performed are directly related to the boiling points at the pressures used, and are well within the scope of knowledge of one skilled in the art.

The yields of HFC-32 from the azeotropic mixture using the process of the present invention far exceed those for conventional distillation. In a preferred embodiment, the yield of HFC-32 from the azeotropic mixture is no less than about 90%, more preferably no less than about 95% and even more preferably no less than about 99%.

Additionally, by using pressures and temperatures in this range, conventional equipment can be used in the above-mentioned process with little or no modification.

The following examples are illustrative of the practice of the present invention.

EXAMPLES

Example 1

This example shows the change in the composition of the CFC-12/HFC-32 with a change in pressure.

The system comprised a distillation unit comprising a two gallon stainless steel reboiler equipped with a SS-316 horizontal (U) two bundle heating coils. Directly mounted to the reboiler was a 2" diameter by 100" packed distillation column containing ¼" protruded metal distillation packing. A vertical shell and tube heat exchanger were mounted on the distillation column and cooled with circular cold methanol from a refrigeration unit. Vapor product from the partial condenser was condensed in a cylinder immersed in dry ice.

To this system crude HFC-32 reaction product containing 0.5 wt. % CFC-12 was added. The column was operated at 14.3 psia at an overhead temperature of −54° C. Distillate collected had a composition of 29 wt. % CFC-12.

In a same distillation column, the reboiler was again charged with crude HFC-32 containing 0.5% CFC-12. In this case, the distillation column was operated at 214 psia at a resultant overhead temperature of 12° C. Distillate collected had a composition of 9.2 wt. % CFC-12. The bottoms product contained 136 ppm CFC-12.

Therefore, a drop in concentration of CFC-12 of almost 20 wt % was observed as the pressure increased from atmospheric to 214 psia.

Example 2

This example illustrates the process of the present invention using a single distillation column wherein the feed is introduced into the low pressure distillation.

A crude HFC-32 product stream containing 0.5 wt % CFC-12 obtained by the fluorination of methylene chloride with anhydrous hydrogen fluoride in the presence of a fluorination catalyst is charged to a distillation column.

The distillation column consists of an Inconel reboiler attached to a 2 inch diameter stainless steel column filled with ¼" protruded ribbon packing made of Monel. A stainless steel condenser is mounted on top of the column. Chilled methanol is pumped to the condenser to provide cooling.

The distillation column is operated at about 14.3 psia, a reflux temperature of about −54° C. and a reboiler temperature of about −50° C. Upon distillation, a distillate containing about 29 wt % CFC-12 is removed at a reflux ratio of about 10:1 until the reboiler CFC-12 content is reduced to about 0.05 wt %.

The distillate is then fed back into the column and distilled again. This time, the pressure in the distillation column is raised to about 214 psia by heating the reboiler using steam and raising the condenser temperature. The reflux and distillate from this second distillation is about 12° C. The distillate from this second distillation has a HFC-32/CFC-12 weight ratio of about 10:1.

Example 3

This example illustrates the process of the present invention using a single distillation column wherein the feed is introduced into the high pressure distillation.

A crude HFC-32 product stream containing 30 wt % CFC-12 obtained by the fluorination of methylene chloride with anhydrous hydrogen fluoride in the presence of a fluorination catalyst is charged to a distillation column.

The distillation column consists of an Inconel reboiler attached to a 2 inch diameter stainless steel column filled with ¼" protruded ribbon packing made of Monel. A stainless steel condenser is mounted on top of the column. Chilled methanol is pumped to the condenser to provide cooling.

The distillation column is operated at about 215 psia, a reflux temperature of about 12° C. and a reboiler temperature of about 16° C. Upon distillation, a distillate containing about 9.2 wt % CFC-115 is removed at a reflux ratio of about 10:1 until the reboiler CFC-12 content is reduced to about 1 wt %.

The distillate is then fed back into the column and distilled again. This time, the pressure in the distillation column is decreased to about 14.3 psia by lowering the heat flow in the reboiler and decreasing the condenser temperature. The reflux and distillate temperatures from this second distillation are about −54° C. The distillate from this second distillation has a HFC-32/CFC-12 weight ratio of about 2.4:1.

Therefore, using the process of the present invention, HFC-32 can be recovered with high yields.

Example 4

The following Example demonstrates the process using a system of multiple distillation columns as shown schematically in FIG. 1.

Crude HFC-32 product stream containing 0.5 wt % CFC-12 obtained by the fluorination of methylene chloride with anhydrous hydrogen fluoride in the presence of a fluorination catalyst is subjected to high pressure (200 psia) distillation (not shown in FIG. 1). This results in a HFC-32/CFC-12 azeotropic distillate containing 9.2 wt % CFC-12.

To a distillation column (C1), similar in structure to the distillation column of Example 2, is fed the azeotropic distillate. The distillation is conducted at 14.3 psia, a reflux temperature of about −54° C. and a reboiler temperature of about 45° C. At such low pressures, the azeotrope is relatively high in CFC-12 concentration. Consequently, the distillate (1) contains a relatively high concentration of CFC-12 (29 wt %). On the other hand, little CFC-12 is left in the bottom, and essentially pure HFC-32 (99.9 wt %) is removed as the bottom (2).

The distillate is then passed to a second distillation column (C2) similar in structure to (C1). The distillation is conducted at 214 psia, a reflux temperature of about 12° C. and a reboiler temperature of about 16° C. At such a high pressure, the amount of CFC-12 in the azeotrope drops dramatically. The azeotrope, now rich in HFC-32, is removed in distillate (3) and is refed to distillation column (C1) for further recovery of HFC-32, while essentially pure CFC-12 (99.8 wt %) is removed as the bottoms (4).

Therefore, using the process of the present invention, HFC-32 can be recovered with high yields.

Example 5

This example illustrate the process of the present invention using more than two distillation columns.

Crude HFC-32 containing 0.5 wt % CFC-12 obtained by the fluorination of methylene chloride with anhydrous hydrogen fluoride in the presence of a fluorination catalyst is fed into a distillation column.

The distillation column consists of an Inconel reboiler attached to a 2 inch diameter stainless steel column filled with ¼" protruded ribbon packing made of Monel. A stainless steel condenser is mounted on top of the column. Chilled methanol is pumped to the condenser to provide cooling.

The distillation is conducted at about 14.3 psia, a reflux temperature of about −54° C. and a reboiler temperature of about −50° C. The distillate is enriched in CFC-12 (29 wt %) while the bottom contains essentially pure HFC-32 (>99.9 wt %).

The distillate is then passed to a second distillation column similar to the first column in structure but operated at high pressure (i.e., about 214 psia), a reflux temperature of about 12° C. and a reboiler temperature of about 16° C. At this pressure, the distillate is enriched in HFC-32 (>91 wt %) while the bottoms contain more CFC-12 (>10 wt %).

The distillate is then fed to a third distillation column similar in structure to the first column and operated at low pressure (i.e., about 14.3 psia), a reflux temperature of about −54° C. and a reboiler temperature of about −50° C. At this pressure, the distillate is becoming enriched in CFC-12 (about 29 wt %) while the bottoms are richer in HFC-32 (>99.9 wt %).

Finally, the distillate from this third distillation is fed to a fourth distillation column similar in structure to the first column but operated at about 214 psia, a reflux temperature of about 12° C., and a reboiler temperature of about 16° C. Under these conditions, HFC-32 (91 wt %) is recovered as distillate while the bottoms are enriched in CFC-12 (>90 wt %).

Therefore, using the process of the present invention, HFC-32 can be recovered with high yields.

What is claimed is:

1. A process for the purification of difluorometane from a mixture of difluoromethane (HFC-32) and dichlorodifluoromethane (CFC-12), said process comprising:
   (a) distilling a first mixture of HFC-32 and CFC-12 at a first pressure below 40 psia in a first distillation step to produce a first distillate and a first bottoms, said first distillate being enriched with CFC-12 and said first bottoms being enriched with HFC-32; and
   (b) distilling the first distillate at a second pressure of about 50 to about 400 psia in a second distillation step to produce a second distillate and a second bottoms, said first distillate having a second mixture of HFC-32 and CFC-12 at said second pressure, the pressure difference between the first and second distillation steps is sufficient to result in a change in composition of an azeotrope of CFC-12 and HFC-32 of at least 10 wt %, said second distillate being enriched with HFC-32, and said second bottoms being enriched with CFC-12;
   (c) recovering purified HFC-32 from said first bottoms; and
   (d) one of either feeding said second distillate to said first distillation step or recovering HFC-32 from said second distillate.

2. The process of claim 1, wherein said second distillate is fed to said first distillation step.

3. The process of claim 1 wherein said first pressure is about 5 to about 30 psia, and said second pressure is about 100 to about 300 psia.

4. The process of claim 1 wherein said first pressure is about atmospheric pressure, and said second pressure is about 175 to about 225 psia.

5. The process of claim 1, wherein the concentration of said CFC-12 in said first mixture is no less than about 0.5 wt %.

6. The process of claim 5, wherein said concentration of CFC-12 in said first mixture is no less than about 9 wt %.

7. A process for the purification of difluoromethane from a mixture of difluoromethane (HFC-32) and dichlorodiflaoromethane (CFC-12), said process comprising:
   (a) distilling a first mixture of HFC-32 and CFC-12 at a first pressure of about 50 to about 400 psia in a first distillation step to produce a first distillate and a first bottoms, said first distillate being enriched with HFC-32 and said first bottoms being enriched with CFC-12; and
   (b) distilling the first distillate at a second pressure of below about 40 psia in a second distillation step to produce at a second distillate and a second bottoms, said first distillate having a second mixture of HFC-32 and CFC-12 at said second pressure, the pressure difference between the first and second distillation steps is sufficient to result in a change in composition of an azeotrope of CFC-12 and HFC-32 of at least 10 wt %, said second distillate being enriched with CFC-12, and said second bottoms being enriched with HFC-32; and (c) recovering purified HFC-32 from said second bottoms.

8. The process of claim 1 or 7, wherein steps (a) and (b) are repeated.

9. The process of claim 1 or 7 wherein said distillation steps are conducted in a single column.

10. The process of claim 1 or 7 wherein said distillation steps are conducted in two separate columns.

11. The process of claim 10 wherein said distillation steps are conducted as batch distillations steps.

12. The process of claim 10 wherein said distillation steps are conducted as a continuous distillation process.

13. The process of claim 1 or 7, wherein the pressure difference between the first and second distillation steps is sufficient to result in a change in composition of the azeotrope of CFC-12 and HFC-32 of at least 20 wt %.

14. The process of claims 1 or 7 in which HFC-32 is recovered with a yield of no less than about 90%.

15. The process of claim 14, wherein the yield is no less than 99%.

16. The process of claim 7 wherein said second pressure is about 5 to about 30 psia, and said first pressure is about 100 to about 300 psia.

17. The process of claim 16 wherein said second pressure is about atmospheric pressure, and said first pressure is about 175 to about 225 psia.

18. The process of claim 7, further comprising:

(d) feeding said second distillate to said first distillation step.

* * * * *